US00PP14533P39

(12) United States Plant Patent
Benardella

(10) Patent No.: US PP14,533 P3
(45) Date of Patent: Feb. 17, 2004

(54) MINIATURE ROSE PLANT NAMED 'BENHILE'

(50) Latin Name: *Rosa minima*
Varietal Denomination: Benhile

(75) Inventor: Frank Benardella, Englishtown, NJ (US)

(73) Assignee: Nor'East Miniature Roses, Inc., Rowley, MA (US)

( * ) Notice: Subject to any disclaimer, the term of this patent is extended or adjusted under 35 U.S.C. 154(b) by 0 days.

(21) Appl. No.: 09/995,055

(22) Filed: Nov. 27, 2001

(65) Prior Publication Data

US 2003/0101490 P1 May 29, 2003

(51) Int. Cl.[7] ..... A01H 5/00
(52) U.S. Cl. ..... Plt./116
(58) Field of Search ..... Plt./116, 123, 121, Plt./128

*Primary Examiner*—Bruce R. Campell
*Assistant Examiner*—June Hwu
(74) *Attorney, Agent, or Firm*—Christie, Parker & Hale, LLP

(57) ABSTRACT

A new and distinct Miniature Rose plant having attractive pink and white flowers.

1 Drawing Sheet

BACKGROUND OF THE INVENTION

The present invention relates to a new and distinct variety of *Rosa minima*. The new variety was created by crossing as seed parent the variety known as 'BENFIG' (U.S. Plant Pat. No. 8,020) and as pollen parent, the variety known as 'BENMAGIC' (U.S. Plant Pat. No. 8,603). The varietal denomination of the new variety is 'BENHILE'.

SUMMARY OF THE INVENTION

Among the novel characteristics possessed by the new variety which distinguishes it from its parents and all other varieties of which I am aware, is its attractive pink flowers.

Asexual reproduction by propagation of vegetative cuttings of the new variety as performed in Essex County, Mass. show that the foregoing and other distinguishing characteristics come true to form and are established and transmitted through succeeding propagation.

COMPARISON WITH PARENTS

The new variety may be distinguished from its parents in flower color and size. The new variety is shorter, more branched and more compact than either of its parents.

Its seed parent, 'BENFIG,' has ivory or very pale pink flowers that are moderately fragrant whereas the flowers of the new variety have white petals with pink edges and fewer petals per flower.

The flowers of the pollen parent, 'BENMAGIC,' has petals that are white with reddish edges whereas the petals of the new variety are white with more pink-toned edges. The new variety has a higher petal count than the pollen parent.

COMPARISON WITH RELATED VARIETIES

The new variety also differs from the variety 'BENMFIG' (Pending U.S. Plant patent application Ser. No. 09/783,455; filed Feb. 14, 2001) which shares both seed and pollen parents. The new variety differs from 'BENMFIG' in habit and bloom. 'BENMFIG' is taller, has fewer petals with a blend of pink tones whereas the new variety is more compact, its petals are bi-colored pink and white only and possess more petals per flower.

The new variety also differs in flower coloration from that of the variety 'SAVACHILD' (U.S. Plant Pat. No. 8,175). 'SAVACHILD' shares 'PARTY GIRL' (U.S. Plant Pat. No. 4,598) in its parentage. 'PARTY GIRL' is in the parentage of the new variety three (3) generations back. The difference between 'SAVACHILD' and 'BENHILE' is that the flowers of the new variety are a deeper shade of pink and possess more than twice the petal count as 'SAVACHILD'.

BRIEF DESCRIPTION OF ILLUSTRATION

The accompanying photograph illustrates a typical specimen of the new variety and shows the flowering thereof from bud to full bloom depicted in color as nearly true as it is reasonably possible to make in a color illustration of this character. Throughout this specification, color references and/or values are based upon The Royal Horticultural Society Colour Chart and terminology used in the color descriptions herein refers to plate numbers in this color chart except where common terms of color definition are employed.

DESCRIPTION OF THE NEW VARIETY

The following observations were made of 3 to 4 year-old plants of the new variety grown indoors, in 1.8 gallon containers, under plastic in Essex County, Mass. during the month of September. Phenotypic expression may vary with environmental, cultural and climatic conditions, as well as differences in conditions of light and soil.

FLOWER

Blooming habit: Recurrent.

*Bud.*—About 1 inch just before sepals divide. Form: Obovate Color: When sepals first divide color near 53C; when petals begin to unfurl, color near 57A inside edges at tip and outside edges, feathering immediately in with the white, near 155A.

*Sepals.*—Lanceolate; extending near ¼ inch beyond tip of bud just before dividing; very finely bearded; 3 having occasional "flags" along both edges; average length about 27/32 inch, average width about 9/32 inch at widest point. Upper Surface: Texture somewhat coarse, color near 146B. Under surface: Texture smooth, color near 146C flushed with white, near 155A.

*Peduncle.*—Length: About 1½ inches. Aspect: Straight. Strength: Erect, very strong. Color: Near 144C; peduncle is covered with fine prickles and hairs.

BLOOM

Size: Average when fully expanded about 2 inches.
Borne: Singly and in small sprays of 2 to 3 blooms.
Form: High centered at first; petals becoming and remaining loosely rolled outward and ruffled at maturity.
Petalage: Between 35 to 48.
Fragrance: Moderate.
Persistence: Between 5 to 8 days only petals drop; peduncle and receptacle remain attached until dead.
Lasting quality: Between 4 to 6 days as cut flower.

PETALS

Texture: Smooth.
Appearance: Inside velvety; outside velvety.
Form: Broad, spatulate, margin entire, slightly notched.
Size: Length about 15/16 inch at point of attachment to tip; outer petal width about 13/16 inch at widest part.
Arrangement: Imbricated, shingle-like; regularly arranged.
Color during first 2 days:

*Inner petals.*—Upper side near 57B along edges feathering into white, near 155A toward center and base to about half way in and down petal then being all white, near 155A; under side between 57B and 57C along edges feathering into white, near 155A.

*Outer petals.*—Upper side near 57A along edges feathering into white, near 155A at center and base of each petal, but only ¼ to ⅓ of the way down; under side very slight edge of near 57B becoming all white, near 155A.

When half-blown:

*Inner petals.*—Upper side near 57B along edges feathering into white, near 155A; under side between 57B and 57C feathering into white, near 155A.

*Outer petals.*—Upper side near 63B feathering immediately into white, near 155A, ¼ to ⅓ of way down and in and becoming all white, near 155A; under side near 65B along outer ⅓ of petal edge and becoming all white, near 155A.

Base of petals (point of attachment): White, near 155A.
General tonality from a distance: Deep pink.
Color change: Slight as bloom ages, becoming only sightly lighter with more purple hues.
General tonality from a distance: Pink and white bi-color even after 3 or more days.
Petaloids in center: Variable up to about 13 petaloids, growing conditions effect number of petaloids, usually warmer temperatures result in increased number of petaloids and decreased number of petals.

*Size.*—Average size between ¼ to ⅝ inch wide at widest part; length from point of attachment between ⅜ and ¾ inch.

*Color.*—Same as inner petals except less of the petaloid is white, near 155A.

*Texture.*—Smooth.

Notable characteristics: Lack of form — as if it can't decide to be a petal or anther; upper edge "center" may have dark yellow semi-oval around light yellow as if starting to form anther. This part of edge of petaloid is recessed considerably from rest of edge causing a very deformed petaloid, looks like upper part of a light yellow anther with a dark yellow pollen along its outer edge but not fully formed.

REPRODUCTIVE ORGANS

Arrangement of stamens, filaments and anthers: Regularly arranged around outer edge of receptacle.
Stamens: Averaging about 90.
Filaments: Length about 3/16 inch; color Light yellow near 8D.
Anthers: Light yellow near 8D.
Pollen: Dark yellow near 17B.
Pistils: About half as many as stamens, about 45.
Styles: Very thin, uneven length; color near 53B.
Stigmas: Near 51C.
Receptacle:

*Shape.*—Urn-shaped; surface texture smooth, glabrous.

*Size.*—Diameter about ⅜ inch.

*Color.*—Near 144A.

Hips:

*Shape.*—Globular.

*Size.*—Diameter up to about ⅝ inch.

*Color.*—Near 162A and near 168C in the sun.

Seeds: Do not protrude; surface texture glabrous; color near 19D.

PLANT

Form: Spreading, upright and compact.
Growth: Vigorous, well branched.
Size: At maturity, height about 13 inches; width between 25 to 27 inches.
Foliage: Pinnately compound of 5 to 7 leaflets; occasionally 3 leaflets.
Size: Mature leaf up to about 4⅜ inches from stem to tip measured along the rachis; average about 3 inches.
Shape: Oval pointed; mature terminal leaflet base to tip up to 1⅞ inches; average 1½ inches.
Quantity: Abundant.
Color:

*New foliage.*—Upper side between 146A and 147A; under side between 146A and 146B.

*Mature foliage.*—Upper side near 147A; under side near 147B.

Texture:

*Upper side.*—Smooth, semi-glossy.

*Under side.*—Coarse, matte.

Edge: Serrated.
Serration: Fine, even.
Stipules: Slightly bearded with the very edge curled under giving the edge a smooth appearance; length from about 11/32 to 26/32 inch; color on mature leaf near 137C; smooth texture.
Petioles: Upper side color near 144C, under side near 145C.
Rachis: Coarse texture, covered with very short and coarse hairs.
Color:

*Mature leaf.*—Upper side color between 144B and 146C; under side near 144A.

*Immature leaf.*—Upper side between 144A and 146B, flushed with 187A in the sun; under side near 144A and 146B flushed with 187C in the sun.

Prickles: Coarse, very short and up to 3 prickles on underside of rachis.

Resistance to disease: Resistance seems good against aphids, average for spider mites; good resistance to Mildew; resistence to Rust or Blackspot not observed.

WOOD

New shoots:

*Bark.*—Smooth.

*Wood.*—Near 146A.

Old wood:

*Bark.*—Smooth.

*Wood.*—Near 137C.

Flowering stem: Length from about 4 inches to 7 inches where born singly; usually about 4½ inches.

Thorns:

*Quantity.*—Ordinary quantity on main stalks from base; few thorns on laterals from stalk.

*Form.*—Curves are angled somewhat downward; irregularly positioned.

*Length.*—Varying from about 1/16 to 4/16 inch.

*Color.*—Immature thorns: Near 39A at the base and very light green at the tip becoming near 160C at the base and near 164A at the tip. Mature thorns: Near 165B.

*Prickles.*—No prickles on main or lateral stalks; some prickles on leaves; color near 160D with the very tip near 165A.

Winter hardiness: Ample winter protection recommended in Zones 5 and colder.

I claim:

1. A new and distinct Miniature Rose plant of the variety substantially as shown and described.

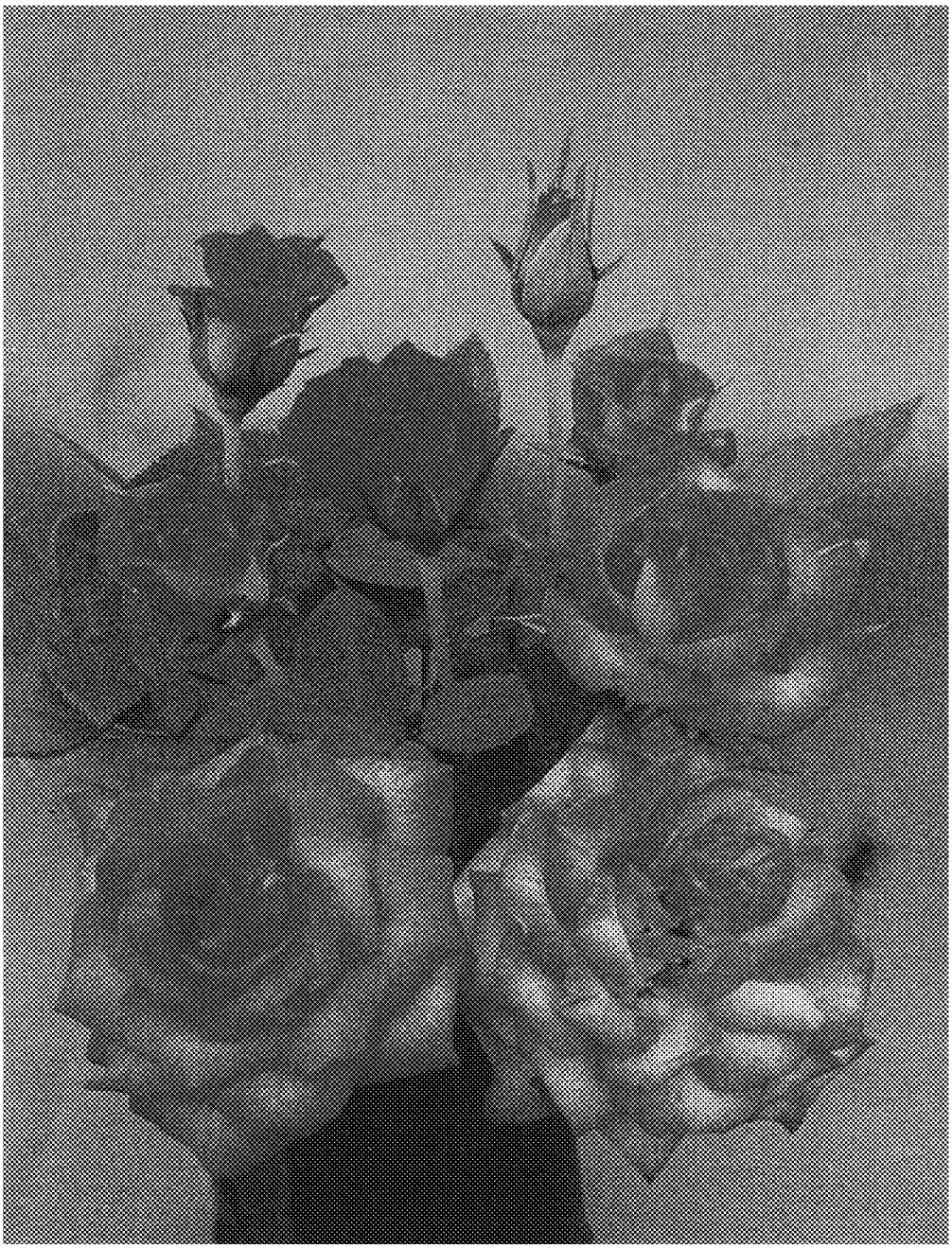

* * * * *